(12) United States Patent
Lee et al.

(10) Patent No.: US 6,887,997 B2
(45) Date of Patent: May 3, 2005

(54) 9H-IMIDAZO[1,2-A]PURIN-9-ONE COMPOUNDS

(75) Inventors: Fang Yu Lee, Taichung (TW); Fang Chen Lee, Taichung (TW); Chang An Yang, Taichung (TW); Ma Wei Yong, Shanghai (CN); Xu Ai Wu, Shanghai (CN); Wu Qiu Ye, Shanghai (CN); Xiao Xu Hua, Shanghai (CN)

(73) Assignee: Yung Shin Pharmaceutical Ind. Co., Ltd., Taipei (TW)

( * ) Notice: Subject to any disclaimer, the term of this patent is extended or adjusted under 35 U.S.C. 154(b) by 0 days.

(21) Appl. No.: 10/161,215

(22) Filed: May 31, 2002

(65) Prior Publication Data

US 2003/0105116 A1 Jun. 5, 2003

Related U.S. Application Data

(60) Provisional application No. 60/295,086, filed on May 31, 2001.

(51) Int. Cl.$^7$ ............................................. C07D 487/14
(52) U.S. Cl. ...................................................... 544/251
(58) Field of Search ........................... 514/267; 544/251

(56) References Cited

U.S. PATENT DOCUMENTS

| | | | |
|---|---|---|---|
| 5,412,088 A | 5/1995 | Jones et al. | |
| 5,521,294 A | 5/1996 | Wildfeuer | |
| 5,591,722 A | 1/1997 | Montgomery et al. | |
| 5,705,630 A | 1/1998 | Ueda et al. | |
| 5,834,609 A | 11/1998 | Horne et al. | |

OTHER PUBLICATIONS

Mann, G.; Hartwig, J. F.; Driver, M. S.; Fernandez–Rivas, C.; J. Am. Chem. Soc.; (Communication); 1998; 120(4); 827–828.*
Remaud, G.; Kjellberg, J.; Johansson, N. G.; Chattopadhyaya, J. Tetrahedron, 43(2), 365–76 (English) 1987.*
Golankiewicz, Bozenna; Ostrowski, Tomasz; Boryski, Jerzy; De Clercq, Erik, Journal of the Chemical Society, Perkin Transactions 1: Organic and Bio–Organic Chemistry (1972–1999) (3), 589–93 (English) 1991.*
Golankiewicz, Bozenna; Ostrowksi, Tomasz; Andrei, Garciela; Snoeck, Robert; De Clercq, Erik, Journal of Medicinal Chemistry 37(19), 3187–90 (English) 1994.*
Boryski, Jerzy; Golankiewicz, Bozenna; De Clercq, Erik, Journal of Medicinal Chemistry, 31(7), 1351–5 (English) 1988.*
Johnson Ji, Decker S, Zaharevitz D, Rubinstein LV, Venditti JM, Schepartz S, Kalyandrug S, Christian M, Arbuck S, Hollingshead M, Sausville EA., Br J Cancer. May 18, 2001;84(10):1424–31.*
Newell DR, Br J Cancer. May 18, 2001;84(10):1289–90.*

Brown JM, Oncol Res. 1997;9(5):213–5.*
Weinstein JN, et al, Science. Jan. 17, 1997;275(5298):343–9.*
Hamburger, Anne W., JNCI, 66 (6), 1981, pp. 981–986.*
Draetta, G. and Pagano, M. in "Annual Reports in Medicinal Chemistry, vol. 31", 1996, Academic Press, San Diego, p 241–246.*
John D. Roberts and Marjorie C. Caserio, "Basic Principles of Organic Chemistry", Benjamin, New York, 1964, p 837.*
Dong et al., "Hydrolysis or carcinogen—DNA adducts by three classes of deoxyribonucleosidase to their corresponding bases," Carcinogenesis 12(6):1125–1128, 1991.
Hanna et al., "A Convenient Synthesis of 2'–Dexoy–6–thioguanosine, Ara–Guanine, . . . Salt Glycosylation Procedure," J. Heterocyclic Chem. 25:1899–1903, 1988.
Gaffney et al., "The Influence of the Purine 2–Amino Group on DNA Conformation and Stability–II," Tetrahedron 40:3–13, 1984.
Golankiewicz et al., "Fluorescent Tricyclic Analogues of Acyclovir and Ganciclovir. A Structure–Antiviral Activity Study," J. Med. Chem. 44:4284–4287, 2001.
Kasai et al., "Structure of Wye (Yt Base) and Wyosine (Yt) from *Torulopsis utilis* Phenylalanine Transfer Ribonucleic Acid," Biochemistry 15(4): 898–904, 1976.
Nair et al., "Determination of the Structure of the Adduct from Guanosine and Glycidaldehyde," Tetrahedron Letters 25 (3):247–250, 1984.
Plavec et al., "Comparative Assessment of Structure and Reactivity of Wyosine by Chemistry, Spectroscopy and *ab initio* Calculations," Tetrahedron 52(5): 1597–1608, 1996.
Zeidler, "7–Alkynylation of Tricyclic Analogues of Acyclovir by the Sonogashira Reaction," Collection Symposium Series 2:31–34, 1999.

* cited by examiner

*Primary Examiner*—Thomas C. McKenzie
(74) *Attorney, Agent, or Firm*—Fish & Richardson P.C.

(57) ABSTRACT

Fused tri-heterocyclic compounds of formula:

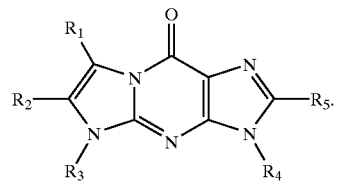

$R_1$ is H or alkyl; $R_2$ is H, alkyl, alkenyl, aryl, heteroaryl, cyclyl, or heterocyclyl; $R^3$ and $R^4$, independently, is H, alkyl, alkenyl, aryl, heteroaryl, cyclyl, heterocyclyl, or $(CR^aR^b)_mX(CR^cR^d)_nY$; in which X is a bond, O, S, or $NR^e$; Y is alkoxy, aryloxy, heteroaryloxy, $OC(O)R^e$, $C(O)R^e$, $N(R^eR^{e'})$, $NR^eC(O)R^{e'}$, $S(O)_2R^e$, or $SR^e$; each of m and n, independently, is 1, 2, 3, 4, or 5; each of $R^a$, $R^b$, $R^c$, $R^d$, $R^e$, and $R^{e'}$, independently, is H, alkyl, aryl, heteroaryl, cyclyl, or heterocyclyl; and $R_5$ is H or halogen.

29 Claims, No Drawings

9H-IMIDAZO[1,2-A]PURIN-9-ONE COMPOUNDS

RELATED APPLICATIONS

This application claims priority to U.S. provisional application No. 60/295,086 filed on May 31, 2001, the contents of which are incorporated herein by reference.

BACKGROUND

The treatment of tumor can be approached by several modes of therapy, including surgery, radiation, chemotherapy, and a combination of any of these treatments. Among them, chemotherapy is indispensable for inoperable or metastatic forms of cancer. Considering the diversity of tumors in terms of cell type, morphology, growth rate, and other cellular characteristics, the U.S. National Cancer Institute (NCI) has developed a "disease-oriented" approach to anti-tumor activity screening. Boyd, M. R. (1989) *In Principle of Practice of Oncology* Devita, J. T., Hellman, S., and Rosenberg, S. A. (Eds.) Vol. 3, PPO Update, No. 10. This in vitro screening system is based on human tumor cell line panels consisting of approximately 60 cell lines of major human tumors (e.g., leukemia, lung cancer, colon cancer, CNS cancer, melanoma, ovarian cancer, renal cancer, prostate cancer, and breast cancer), and serves as a tool for identifying compounds that possess anti-tumor activities. Among the compounds, modified nucleobases are of particular interest.

SUMMARY

This invention is based on the discovery of certain fused tricyclic analogues of guanosine, a nucleobase, for treating tumor.

An aspect of the present invention relates to fused tri-heterocyclic compounds of the formula:

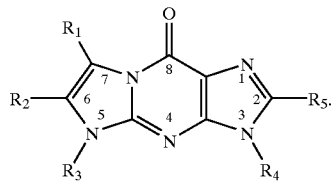

$R_1$ is H or alkyl; $R_2$ is H, alkyl, alkenyl, aryl, heteroaryl, cyclyl, or heterocyclyl; $R_3$ and $R_4$, independently, is H, alkyl, alkenyl, aryl, heteroaryl, cyclyl, heterocyclyl, or $(CR^aR^b)_mX(CR^cR^d)_nY$; in which X is a bond, O, S, or $NR^e$; Y is alkoxy, aryloxy, heteroaryloxy, $OC(O)R^e$, $C(O)R^e$, $N(R^eR^{e'})$, $NR^eC(O)R^{e'}$, $S(O)_2R^e$, or $SR^e$; each of m and n, independently, is 1, 2, 3, 4, or 5; each of $R^a$, $R^b$, $R^c$, $R^d$, $R^e$, and $R^{e'}$, independently, is H, alkyl, aryl, heteroaryl, cyclyl, or heterocyclyl; and $R_5$ is H or halogen. Note that the left atom shown in any substituted group described above is closest to the tri-heterocyclic ring. A subset of the just-described compounds is featured by that $R_4$ is $(CR^aR^b)_mX(CR^cR^d)_nY$; $R_1$ is H; $R_2$ is alkyl or aryl; $R_3$ is alkyl, alkenyl, or aryl; and $R_5$ is H. Another subset is featured by that $R_4$ is alkyl, alkenyl, or aryl; $R_1$ is H; $R_2$ is alkyl or aryl; $R_3$ is alkyl, alkenyl, or aryl; and $R_5$ is H. Preferably, each of $R^a$, $R^b$, $R^c$, and $R^d$ is H; X is O; and Y is $OC(O)R^e$.

Another aspect of the present invention relates to fused tri-heterocyclic compounds also covered by the above formula, wherein $R_1$ is H or alkyl; $R_2$ is H, alkyl, alkenyl, heteroaryl, cyclyl, or heterocyclyl; $R_3$ is H, alkyl, alkenyl, aryl, heteroaryl, cyclyl, heterocyclyl, or $(CR^aR^b)_mX(CR^cR^d)_nY$; $R_4$ is $(CR^aR^b)_mX(CR^cR^d)_nY$, in which X is a bond, O, S, or $NR^e$; Y is OH; each of m and n, independently, is 1, 2, 3, 4, or 5; each of $R^a$, $R^b$, $R^c$, and $R^d$, independently, is H, alkyl, aryl, heteroaryl, cyclyl, or heterocyclyl; and $R_5$ is H or halogen. A subset of the compounds is featured by $R_1$ is H; $R_2$ is alkyl; wherein $R_3$ is alkyl, alkenyl, or aryl; and $R_5$ is H. Preferably, each of $R^a$, $R^b$, $R^c$, and $R^d$ is H; and X is O.

Also within the scope of the present invention are fused tri-heterocyclic compounds covered by the above formula, wherein $R_1$ is H or alkyl; $R_2$ is H, alkyl, alkenyl, aryl, heteroaryl, cyclyl, or heterocyclyl; $R_3$ is H, alkenyl, aryl, heteroaryl, cyclyl, heterocyclyl, or $(CR^aR^b)_mX(CR^cR^d)_nY$; $R_4$ is $(CR^aR^b)_mX(CR^cR^d)_nY$, in which X is a bond, O, S, or $NR^e$; Y is OH; and each of m and n, independently, is 1, 2, 3, 4, or 5; each of $R^a$, $R^b$, $R^c$, $R^d$, $R^e$, and $R^{e'}$, independently, is H, alkyl, aryl, heteroaryl, cyclyl, or heterocyclyl; and $R_5$ is H or halogen. A subset of the compounds is featured by $R_1$ is H; $R_2$ is alkyl or aryl; $R_3$ is alkenyl or aryl; $R_5$ is H; each of $R^a$, $R^b$, $R^c$, and $R^d$ is H; and X is O.

Alkyl, alkenyl, aryl, heteroaryl, cyclyl, and heterocyclyl mentioned herein include both substituted and unsubstituted moieties. The term "substituted" refers to one or more substituents (which may be the same or different), each replacing a hydrogen atom. Examples of substituents include, but are not limited to, halogen, hydroxyl, amino, cyano, nitro, $C_1$~$C_6$ alkyl, $C_1$~$C_6$ alkenyl, $C_1$~$C_6$ alkoxy, aryl, heteroaryl, or heterocyclyl, wherein alkyl, alkenyl, alkoxy, aryl, heteroaryl and heterocyclyl are optionally substituted with $C_1$~$C_6$ alkyl, aryl, heteroaryl, halogen, hydroxyl, amino, alkylamino, arylamino, dialkylamino, diarylamino, cyano, or nitro. Note that combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject or antiseptic, wound dressing impregnation, sterilizant, or disinfectant applications).

The term "alkyl" refers to both linear and branched alkyl containing 1 to 6 carbons. The term "cyclyl" refers to a hydrocarbon ring containing 4 to 8 carbons. The term "heterocyclyl" refers to a ring containing 4 to 8 ring members that have at least one heteroatom (e.g., S, N, or O) as part of the ring. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, fluorenyl, pyrrolyl, thienyl, oxazolyl, imidazolyl, thiazolyl, pyridinyl, pyrimidinyl, quinazolinyl, and indolyl.

The fused tri-heterocyclic compounds described above include the compounds themselves, as well as their salts and their prodrugs, if applicable. Such salts, for example, can be formed between a positively charged substituent (e.g., amino) on a fused tri-heterocyclic compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a fused tri-heterocyclic compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing fused tri-heterocyclic compounds described above.

This invention also relates to a method for treating tumor (e.g., leukemia, lung cancer, colon cancer, CNS cancer, melanoma, ovarian cancer, renal cancer, prostate cancer, or breast cancer). The method includes administering to a subject in need thereof an effective amount of the compound having the above formula, wherein $R_1$ is H or alkyl; $R_2$ is H, alkyl, alkenyl, aryl, heteroaryl, cyclyl, or heterocyclyl; $R_3$ and $R_4$, independently, is H, alkyl, alkenyl, aryl, heteroaryl, cyclyl, heterocyclyl, or $(CR^aR^b)_mX(CR^cR^d)_nY$; in which X is a bond, O, S, or $NR^e$; Y is $OR^e$, $OC(O)R^e$, $C(O)R^e$, $N(R^eR^{e'})$, $NR^eC(O)R^{e'}$, $S(O)_2R^e$, or $SR^e$; and each of m and n, independently, is 1, 2, 3, 4, or 5; each of $R^a$, $R^b$, $R^c$, $R^d$, $R^e$, and $R^{e'}$, independently, is H, alkyl, aryl, heteroaryl, cyclyl, or heterocyclyl; and $R_5$ is H or halogen. Referring to the above formula, a subset of the compounds is featured by that $R_4$ is $(CR^aR^b)_mX(CR^cR^d)_nY$; $R_1$ is H; $R_5$ is H; each of $R^a$, $R^b$, $R^c$, and $R^d$ is H; X is O; and Y is $OR^e$ or $OC(O)R^e$. Another subset is featured by that $R_4$ is alkyl, alkenyl, or aryl; $R_1$ is H; $R_5$ is H; and $R_3$ is alkyl, alkenyl, or aryl.

Also within the scope of this invention are a composition containing one or more of the fused tri-heterocyclic compounds described above for use in treating tumor, and the use of such a composition for the manufacture of a medicament for tumor treatment.

Other features or advantages of the present invention will be apparent from the following detailed description of several embodiments, and also from the appending claims.

DETAILED DESCRIPTION

Seven exemplary fused tri-heterocyclic compounds of this invention are 3-(2-hydroxy-ethoxymethyl-6-(2-methylpropanyl)-3,5-dihydro-1,3,4,5,7a-pentaaza-s-indacen-8-one (compound 1); 3-(2-hydroxy-ethoxymethyl)-6-(5-chloro-thiophen-2-yl)-3, 5-dihydro-1,3,4,5,7a-pentaaza-s-indacen-8-one (compound 2); 3-(2-acetoxy-ethoxymethyl)-6-(4-chlorophenyl)-3, 5-dihydro-1,3,4,5,7a-s-indacen-8-5-(4-methoxyphenylmethyl)-3-(2-hydroxy-ethoxymethyl)-6-(4-bromophenyl)-3,5-dihydro-1,3,4,5,7a-pentaaza-s-indacen-8-one (compound 4); 5-(2-ethanitrilyl)-3-(2-acetoxy-ethoxymethyl)-6-phenyl-3,5-dihydro-1,3,4,5,7a-pentaaza-s-indacen-8-one (compound 5); 5-(3,4-dichlorophenylmethyl)-3-(2-acetoxy-ethoxymethyl)-6-(4-chlorophenyl)-3,5-dihydro-1,3,4,5,7a-s-indacen-8-one (compound 6); and 3,5-dibenzyl-6-(4-chlorophenyl)-3,5-dihydeo-1,3,4,5,7a-pentaaza-s-indacen-8-one (compound 7).

The fused tri-heterocyclic compounds described above can be prepared by methods well known in the art, as well as by the synthetic routes disclosed herein. For example, one can react 9-[(2-hydroxyethoxy)methyl]guanine (acyclovir) with a halogen-substituted ketone to produce a compound of this invention such as compounds 1 and 2. The obtained compound can react with an alkylhalide to produce a desired compound 4. Alternatively, it can react with an anhydride, such as acetic anhydride, to produce another compound of this invention such as compound 3, followed by treatment with an alkylhalide under different conditions to produce a still another compound of this invention such as compounds 5, 6, and 7.

Shown below is a scheme that depicts the synthesis of seven fused tri-heterocyclic compounds.

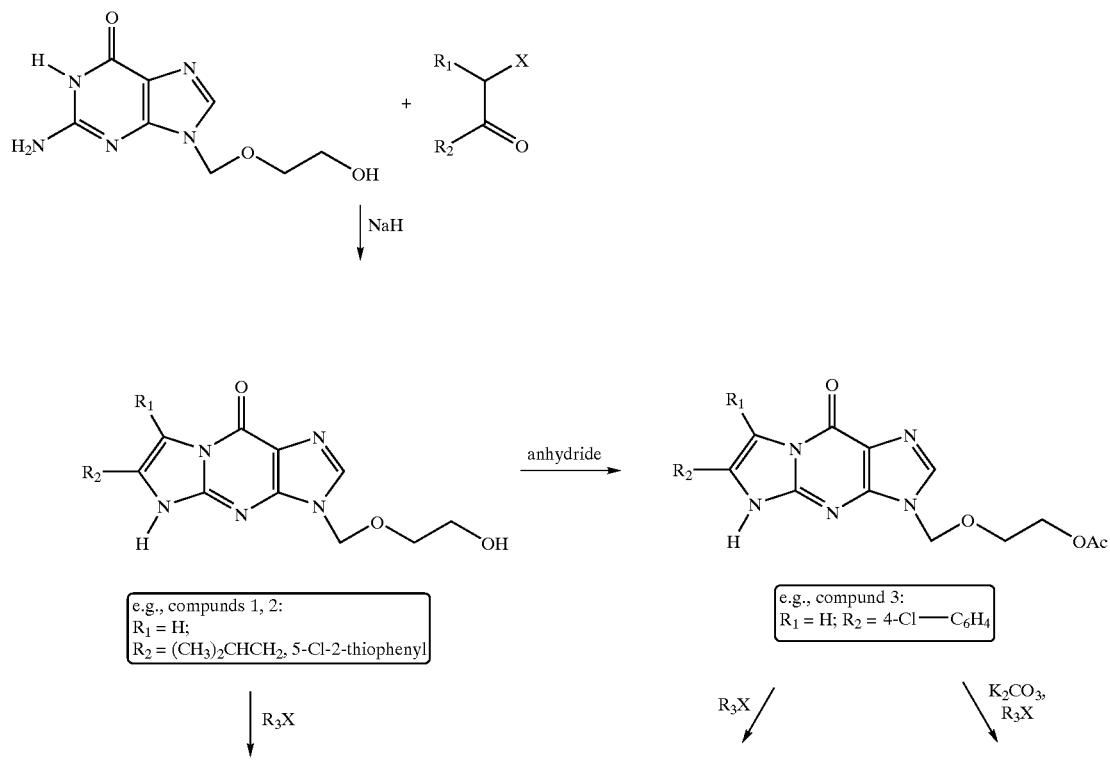

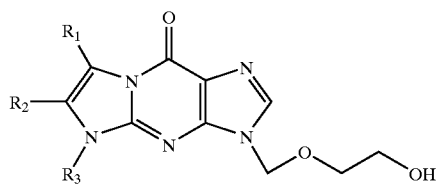

e.g., compund 4:
$R_1 = H$;
$R_2 = 4\text{-Br}\text{—}C_6H_4$; and
$R_3 = 4\text{-CH}_3O\text{—}C_6H_4\text{—}CH_2$

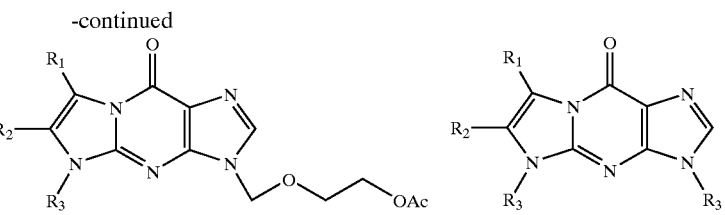

e.g., compunds 5, 6:
$R_1 = H$;
$R_2 = C_6H_5, 4\text{-Cl}\text{–}C_6H_4$
$R_3 = CH_2CN, 3,4\text{-Cl}_2\text{–}C_6H_3\text{—}CH_2$ e.g., compund 7:
$R_1 = H$;
$R_2 = 4\text{-Cl-}C_6H_4$;
$R_3 = C_6H_5CH_2$, Details of synthesis of compounds 1–7 are described, respectively, in Examples 1–7 below.

The chemicals used in the above-described synthetic routes may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the tri-heterocyclic compounds. In addition, various synthetic steps may be performed in an alternate sequence or order to give the desired compounds. Synthetic chemistry transformations and protecting group methodologies (protection and deprotection) useful in synthesizing applicable tri-heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis, 2$^{nd}$ Ed.*, John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A tri-heterocyclic compound thus synthesized can be further purified by a method such as column chromatography, high pressure liquid chromatography, or recrystallization.

Also within the scope of this invention is a pharmaceutical composition that contains an effective amount of one or more of the fused tri-heterocyclic compounds described above and a pharmaceutically acceptable carrier. Further, the present invention covers a method of administering an effective amount of such a compound to a subject in need of tumor treatment. The term "treating" is defined as the application or administration of a composition including the tri-heterocyclic compound to a subject, who has tumor, a symptom of the tumor, a disease or disorder secondary to the tumor, or a predisposition toward the tumor, with the purpose to cure, alleviate, relieve, remedy, or ameliorate the tumor, the symptom of the tumor, the disease or disorder secondary to the tumor, or the predisposition toward the tumor. "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the fused tri-heterocyclic compounds can range from about 5 mg/Kg to about 600 mg/Kg. Effective doses will also vary, as recognized by those skilled in the art, depending on the types of tumors treated, route of administration, excipient usage, and the possibility of co-usage with other therapeutic treatments such as use of other anti-tumor agents or radiation therapy.

To practice the method of the present invention, a fused tri-heterocyclic compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A fused tri-heterocyclic compound can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the fused tri-heterocyclic compounds, or one or more solubilizing agents, can be utilized as pharmaceutical excipients for delivery of the fused tri-heterocyclic compounds. Examples of other carriers include colloidal silicon dioxide, magnesium stearate, cellulose, sodium lauryl sulfate, and D&C Yellow #10.

Fused tri-heterocyclic compounds can be preliminarily screened for their efficacy in treating tumor by in vitro assay based on the NCI screening system, which involves the use of approximately 60 cell lines of major human tumors. See Monks, et al. (1991) JNCI, *J. Natl. Cancer Inst.* 83: 757–766; Alley, et al. (1988) *Cancer Res.* 48: 589–601; Shoemaker, et al. (1988) *Prog. Clin. Biol. Res.* 276: 265–286; and Stinson, et al. (1989) *Proc. Am. Assoc. Cancer Res.* 30: 613. Briefly, a cell suspension that is diluted according to the particular cell type and the expected target cell density (5,000–40,000 cells per well based on cell growth characteristics) is added (100 μL) into a 96-well microtiter plate. A pre-incubation is preformed at 37° C. for 24 hr. Dilutions at twice of an intended test concentration are added at time zero in 100 μL aliquots to each well of the microtiter plate. Usually, a test compound is evaluated at five 10-fold dilutions. In a routine testing, the highest concentration of the test compound is $10^{-4}$ M. Incubations are performed for 48 hr in 5% $CO_2$ atmosphere and 100% humidity. The cells are assayed by using the sulforhodamine B assay described by Rubinstein, et al. (1990, JNCI, *J. Natl. Cancer Inst.* 82: 1113–1118) and Skehan, et al. (1990, JNCI, *J. Natl. Cancer Inst.* 82: 1107–1112). A plate reader is used to read the optical densities and a microcomputer processes the optical densities into the special concentration parameters. The NCI has renamed an $IC_{50}$ value, the concentration that causes 50% growth inhibition, a $GI_{50}$ value to emphasize the correction for the cell counted at time zero; thus, the $GI_{50}$ measures the growth inhibitory power of the test compound. See Boyd, et al. (1992) In *Cytotoxic Anticancer Drugs: Models and Concepts for Drug Discovery and Development;* Vleriote, F. A.; Corbett, T. H.; Baker, L. H. (Eds.); Kluwer Academic: Hingham, MA pp 11–34.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Synthesis of 3-(2-hydroxy-ethoxymethyl-6-(2-methylpropanyl)-3,5-dihydro-1,3,4,5,7a-pentaaza-s-indacen-8-one (compound 1)

A solution of 676 mg a 9-[(2-hydroxyethoxy)methyl] guanine (acyclovir), 18 mL N,N-dimethylformamide (DMF), and 200 mg sodium hydride (80%) was stirred at room temperature for 15 min, then 0.7 mL 4-methyl-1-bromopentan-2-one was added dropwise into the solution. Changing to dark-brown color, the solution was stirred at room temperature for 3 hr, added 15 mL ammonia, and was continuously stirred overnight. The solvent was removed to obtain a residue, which was purified by column chromatography (silica gel) with an elute of chloroform/methanol (6/1) to obtain an oil. Recrystallization of the oil produced compound 1.

$^1$H NMR (400 MHz, $d_6$-DMSO): δ 8.01 (1H, s, NCH=N); δ 7.73 (1H, s, N=CH—C); δ 5.60 (2H, s, NCH$_2$O); δ 4.65 (1H, broad, OH); δ 3.42~3.49 (4H, m, CH$_2$CH$_2$); δ 2.40~2.52 (2H, m, CH$_2$); δ 1.80~1.84 (1H, m, CH); and δ 0.92 (6H, m, 2CH$_3$).

EXAMPLE 2

Synthesis of 3-(2-Hydroxy-ethoxymethyl)-6-(5-chloro-thiophen-2-yl)-3,5-dihydro-1,3,4,5,7a-pentaaza-s-indacen-8-one (compound 2)

A solution of 720 mg acyclovir, 20 mL DMF, and 300 mg sodium hydride (80%) was stirred at room temperature for 30 min, then 2.63 g (11 mmol) 2'-bromo-aceto(5-chloro-thiophenone) was added into the solution. The solution was stirred at room temperature for 3.5 hr, added 50 mL of ammonia, and continuously stirred overnight. The solvent was removed to obtain a residue, which was washed with 10 mL water. The obtained residue was washed again with water and dissolved in ether. The ether solution was dried and purified by column chromatography (silica gel) with an elute of chloroform/ethanol (4/1) to obtain a product of 400 mg. The combined solid, compound 2, was 1.4 g (yield 38.5%, mp. 226–228° C.).

$^1$H NMR (400 MHz, $d_6$-DMSO): δ 8.03 (1H, S, N—CH=N); δ 8.01 (1H, S, N—CH=C); δ 7.45 (1H, d, J=4.0 Hz, thiophene ring); δ 7.20 (1H, d, J=4.0Hz, thiophene ring); δ 5.48 (2H, S, N—CH$_2$—O); and δ 3.54~3.34 (4H, m, —O—CH$_2$—CH2—O—).

HRMS $C_{14}H_{12}ClN_5O_3S$: calculated 365.03464, obtained 365.034922.

EXAMPLE 3

Synthesis of 3-(2-acetoxy-ethoxymethyl)-6-(4-chlorophenyl)-3,5-dihydro-1,3,4,5,7a-s-indacen-8-one (compound 3)

A solution of 1.4 g (6.22 mmol) acyclovir, 30 mL DMF, and 400 mg sodium hydride (80%) was stirred at room temperature for 30 min, then 0.7 mL 2-bromo-4'-chloroacetophenone was added dropwise into the solution. Changing to orange color, the solution was added 17 mL ammonia, and continuously stirred for 5 hr. The solvent was removed to obtain a residue, which was washed with water. The product, 3-(2-hydroxy-ethoxymethyl)-6-(4-chlorophenyl)-3,5-dihydro-1,3,4,5,7a-pentaaza-s-indacen-8-one, was produced and weighted 1.62 g (white solid, yield 72%).

A solution of 1.25 g (3.49 mmol) of the compound thus obtained, 3.5 mL acetic anhydride, and 17.5 mL pyridine was stirred at room temperature overnight, and then concentrated. A 26.5 mL mixture of pyridine/water/methanol (1/1/1) was added, and stirred at room temperature for 4 hr. After the solvent was removed, 60 mL toluene was added and concentrated. Chloroform was added and concentrated to obtain a residue. Recrystallization of the residue from ethyl acetate/ethanol (2/1) produced a white product, compound 3, 1.36 g (yield 97.4%).

EXAMPLE 4

Synthesis of 5-(4-methoxyphenylmethyl)-3-(2-hydroxy-ethoxymethyl)-6-(4-bromophenyl) -3,5-dihydro-1,3,4,5,7a-pentaaza-s-indacen-8-one (compound 4)

A solution of 2.7 g acyclovir, 70 mL DMF, and 800 mg sodium hydride (80%) was stirred at room temperature for 15 min, then 4 g 2,4'-dibromo-acetophenone was added into the solution. The solution was stirred at room temperature for 3 hr, added 15 mL ammonia, and was continuously stirred overnight. The solvent was removed to obtain a residue, which was washed with 50 mL of water and acetone to produce a product, 3-(2-hydroxy-ethoxymethyl)-6-(4-bromophenyl)-3,5-dihydro-1,3,4,5,7a-pentaaza-s-indacen-8-one, 2.55 g (yellow, yield 53%).

A solution of 800 mg of the compound thus obtained, 400 mg potassium carbonate, 50 mL DMF, and 0.35 mL of 4-methoxybenzyl chloride, was stirred at 100° C. for 18 hr. The solution was concentrated to obtain a residue, which was dissolved in methanol and purified by column chromatography (silica gel) with an elute of chloroform/methanol (20/1) to obtain compound 4 of 50 mg (yield 9.6%).

Element analysis C, H, N (%): calculated, 53.15, 4.46, 12.91; found, 53.19, 3.99, 12.85.

EXAMPLE 5

Synthesis of 5-(2-ethanitrilyl)-3-(2-acetoxy-ethoxymethyl)-6-phenyl-3,5-dihydro-1,3,4,5,7a-pentaaza-s-indacen-8-one (compound 5)

A solution of 9.0 g (40 mmol) acyclovir, 200 mL DMF, and 2.8 g sodium hydride (80%) was stirred at room temperature for 30 min, and then 9.6 g 2-bromoacetophenone was added into the solution. After stirring at room temperature for 5 hr, the solution was added 160 mL ammonium, and stirred overnight. The solvent was removed to obtain a solid, which was washed with 50 mL water and 30 mL ethanol. The solid was filtered out, washed with acetone, and weighted 8.0 g (yield 64%).

A solution of 8.0 g (22.5 mmol) of the compound thus obtained [3-(2-hyhoxy-ethoxymethyl)-6-phenyl-3,5-dihydro-1,3,4,5,7a-pentaza-s-cindacen-8-one], 24 mL acetic anhydride, and 120 mL pyridine was stirred at room temperature for 5 hr, and then concentrated to obtain a solid, which was washed with 80 mL toluene. The solid was filtered out, washed with ethyl acetate and small amount of ethanol, and weighted 8.47 g (yield 99%).

A solution of 732 mg of the compound thus obtained (3-(2-acetoxy-ethoxymethyl)-6-phenyl-3,5-dihydro-1,3,4,5,7a-pentaaza-s-indacen-8-one), 552 mg potassium carbonate, 60 mL DMF, and 0.5 mL chloroacetonitrile was stirred at 75° C. for 3.5 hr. After the solvent was removed, 100 mL chloroform was added, and precipitate was formed. The precipitate was filtered out, and the solvent was removed to obtained a residue, which was purified by column chromatography (silica gel) with an elute of chloroform/methanol (50/1) to obtain compound 5 of 310 mg.

$^1$H NMR (400 MHz, $d_6$-DMSO): $\delta$ 8.08 (1H, s NC$\underline{H}$=N); $\delta$ 7.73(1H, s, N=C$\underline{H}$—C); $\delta$ 7.68~7.55 (5H, m, benzen ring); $\delta$ 5.67 (2H, s, NC$\underline{H}_2$O); $\delta$ 5.14 (2H, s, NC$\underline{H}_2$CN); $\delta$ 4.22~3.84 (4H, m, C$\underline{H}_2$C$\underline{H}_2$); and $\delta$ 2.04 (3H, s, C$\underline{H}_3$).

Element analysis C, H, N (%): calculated, 57.83, 4.58, 20.24; found, 57.61, 4.33, 20.46.

EXAMPLE 6

Synthesis of 5-(3,4-dichlorophenylmethyl)-3-(2-acetoxy-ethoxymethyl)-6-(4-chlorophenyl) -3,5-dihydro-1,3,4,5,7a-s-indacen-8-one (compound 6)

A solution of 800 mg compound 3, 400 mg potassium carbonate, 50 mL DMF, and 423 mg 3,4-dichlorobenzyl chloride was stirred at 100° C. for 18 hr. The solvent was removed to obtain a product, compound 6, 150 mg (yield 13.4%).

$^1$H NMR (400 MHz, CDCl$_3$): $\delta$ 7.84 (1H, s NC$\underline{H}$=N), $\delta$ 7.72 (1H, s, N=C$\underline{H}$—C), $\delta$ 7.47 (2H, d, benzen ring, J=8.5 Hz), $\delta$ 7.36 (2H, d, benzen ring, J=8.5 Hz), $\delta$ 7.29 (1H, d, benzen ring, J=2.5 Hz), $\delta$ 7.22 (1H, d, benzen ring, J=2.0 Hz), $\delta$ 6.87 (1H, dd, benzen ring, J=2.5 Hz, J=2.0 Hz), $\delta$ 5.55 (2H, s, NC$\underline{H}_2$O), $\delta$ 5.23 (2H, s, C$\underline{H}_2$C$_6$H$_5$), $\delta$ 4.22~3.84 (4H, m, C$\underline{H}_2$C$\underline{H}_2$), and $\delta$ 2.04(3H, s, C$\underline{H}_3$).

EXAMPLE 7

Synthesis 3,5-dibenzyl-6-(4-chlorophenyl)-3,5-dihydeo-1,3,4,5,7a-pentaaza-s-indacen-8-one (Compound 7)

A solution of 1.6 g (4.0 mmol) of compound 3, 700 mg potassium carbonate, and 140 mL DMF was stirred at room temperature for 30 min. Then 1.3 mL of benzyl bromide was added to the solution. The solution was stirred at 75° C. for 3.5 hr, and concentrated. 150 mL of chloroform was added and stirred for 15 min. The non-soluble particles were removed and washed with additional chloroform. The combined chloroform solution was concentrated to obtain a residue, which was purified by column chromatography (silica gel) with an elute of chloroform/toluene/acetone/methanol (60/20/3/1) to obtain compound 7 of 100 mg (yield 5%).

HRMS $C_{27}H_{20}ClN_5O$: calculated, 465.1351; found, 465.1356.

$^1$H NMR (400 MHz, CDCl$_3$): $\delta$ 8.11 (1H, s NC$\underline{H}$=N); $\delta$ 7.60 (1H, s, N=C$\underline{H}$—C); $\delta$ 7.43~7.04 (9H, d, benzen ring,); $\delta$ 5.55 (2H, s, C$\underline{H}_2$C$_6$H$_5$); and $\delta$ 5.34 (2H, s, C$\underline{H}_2$C$_6$H$_5$).

EXAMPLE 8

Screening for Anti-tumor Activities (NCI Cell Lines).

The cytotoxic activities of a number of fused tri-heterocyclic compounds described above were measured against a panel of 60 different NCI human tumor cell lines.

All test compounds were found to be active against more than one cell line. Indeed, the least potent compound exhibited GI$_{50}$ values <$10^{-4}$ M for as many as 50 cell lines. The most potent compound exhibited GI$_{50}$ values about $10^{-6}$ M also for as many as 50 cell lines.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous the fused tri-heterocyclic compounds of this invention also can be made, screened for their anti-tumor activities, and used to practice this invention. Thus, other embodiments are also within the claims.

What is claimed is:

1. A compound having the following formula:

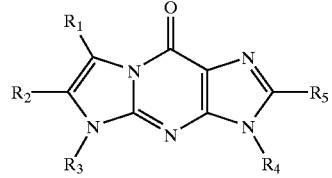

wherein

R₁ is H or alkyl;

R₂ is $C_{2-6}$ alkyl, alkenyl, aryl, heteroaryl, cyclyl, or heterocyclyl;

R₃ is alkyl, alkenyl, cyclyl, heterocyclyl, or $(CR^aR^b)_mX(CR^cR^d)_nY$; in which X is a bond, O, S, or $NR^e$; Y is alkoxy, aryloxy, heteroaryloxy, $OC(O)R^e$, $C(O)R^e$, $N(R^eR^{e'})$, $NR^eC(O)R^{e'}$, $S(O)_2R^e$, or $SR^e$; each of m and n, independently, is 1,2,3,4, or 5; each of $R^a$, $R^b$, $R^c$, $R^d$, $R^e$, and $R^{e'}$, independently, is H, alkyl, aryl, heteroaryl, cyclyl, or heterocyclyl;

R₄ is H, alkyl, alkenyl, cyclyl, heterocyclyl, or $(CR^aR^b)_mX(CR^cR^d)_nY$; in which X is a bond, O, S, or $NR^e$; Y is alkoxy, aryloxy, heteroaryloxy, $OC(O)R^e$, $C(O)R^e$, $N(R^eR^{e'})$, $NR^eC(O)R^{e'}$, $S(O)_2R^e$, or $SR^e$; each of m and n, independently, is 1,2,3,4, or 5; each of $R^a$, $R^b$, $R^c$, $R^d$, $R^e$, and $R^{e'}$, independently, is H, alkyl, aryl, heteroaryl, cyclyl, or heterocyclyl; and R₅ is H or halogen.

2. The compound of claim 1, wherein R₄ is $(CR^aR^b)_mX(CR^cR^d)_nY$.

3. The compound of claim 2, wherein each of $R^a$, $R^b$, $R^c$, and $R^d$ is H, X is O, and Y is $OC(O)R^e$.

4. The compound of claim 2, wherein $R^2$ is $C_{2-6}$ alkyl or aryl.

5. The compound of claim 2, wherein $R^3$ is alkyl or alkenyl.

6. The compound of claim 2, wherein R₅ is H.

7. The compound of claim 6, wherein R₁ is H.

8. The compound of claim 7, wherein R₂ is $C_{2-6}$ alkyl or aryl.

9. The compound of claim 8, wherein R₃ is alkyl or alkenyl, each of $R^a$, $R^b$, $R^c$, and $R^d$ is H, X is O, and Y is $OC(O)R^e$.

10. The compound of claim 1, wherein R₄ is alkyl or alkenyl.

11. The compound of claim 10, wherein R₂ is $C_{2-6}$ alkyl or aryl.

12. The compound of claim 10, wherein R₃ is alkyl or alkenyl.

13. The compound of claim 10, wherein R₅ is H.

14. The compound of claim 13, wherein R₁ is H.

15. The compound of claim 14, wherein R₂ is $C_{2-6}$ alkyl or aryl.

16. The compound of claim 15, wherein R₃ is alkyl or alkenyl.

17. The compound of claim 14, wherein R₃ is alkyl or alkenyl.

18. A compound having the following formula:

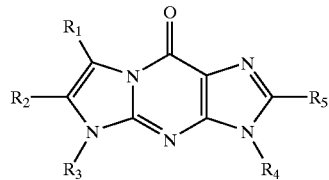

wherein

R₁ is H or alkyl;

R₂ is $C_{2-6}$ alkyl, alkenyl, heteroaryl, cyclyl, or heterocyclyl;

R₃ is $C_{2-6}$ alkyl, alkenyl, cyclyl, heterocyclyl, or $(CR^aR^b)_mX(CR^cR^d)_nY$;

R₄ is $(R^aR^b)_mX(CR^cR^d)_nY$ in which X is a bond, O, S, or $NR^e$; Y is OH; each of m and n, independently, is 1,2,3,4, or 5; each of $R^a$, $R^b$, $R^c$, $R^d$, and $R^e$ independently, is H, alkyl, aryl, heteroaryl, cyclyl, or heterocyclyl; and R₅ is H or halogen.

19. The compound of claim 18, wherein each of $R^a$, $R^b$, $R^c$, and $R^d$ is H, and X is O.

20. The compound of claim 18, wherein R₅ is H.

21. The compound of claim 20, wherein R₁ is H.

22. The compound of claim 21, wherein R₂ is $C_{2-6}$ alkyl.

23. The compound of claim 22, wherein R₃ is $C_{2-6}$ alkyl or alkenyl, each of $R^a$, $R^b$, $R^c$, and $R^d$ is H, and X is O.

24. A compound having the following formula:

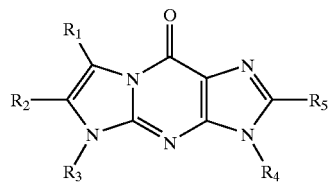

wherein

R₁ is H or alkyl;

R₂ is H, alkyl, alkenyl, aryl, heteroaryl, cyclyl, or heterocyclyl;

R₃ is alkenyl, heterocyclyl, or $(CR^aR^b)_mX(CR^cR^d)_nY$;

R₄ is $(CR^aR^b)_mX(CR^cR^d)_nY$, in which X is a bond, O, S, or $NR^e$; Y is OH; and each of m and n, independently, is 1,2,3,4, or 5; each of $R^a$, $R^b$, $R^c$, $R^d$, $R^e$, and $R^{e'}$, independently, is H, alkyl, aryl, heteroaryl, cyclyl, or heterocyclyl; and R₅ is H or halogen.

25. The compound of claim 24, wherein each of $R^a$, $R^b$, $R^c$, and $R^d$ is H, and X is O.

26. The compound of claim 24, wherein R₅ is H.

27. The compound of claim 26, wherein R₁ is H.

28. The compound of claim 27, wherein R₂ is alkyl or aryl.

29. The compound of claim 28, wherein R₃ is alkenyl, each of $R^a$, $R^b$, $R^c$ and $R^d$ is H, and X is O.

* * * * *